United States Patent
Ternes et al.

(10) Patent No.: US 10,463,861 B2
(45) Date of Patent: Nov. 5, 2019

(54) MANAGED PACE RECHARGE IN A MULTIPOINT PACING SYSTEM

(71) Applicant: Cardiac Pacemakers, Inc., St. Paul, MN (US)

(72) Inventors: David J. Ternes, Roseville, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 500 days.

(21) Appl. No.: 15/040,483

(22) Filed: Feb. 10, 2016

(65) Prior Publication Data

US 2016/0228708 A1 Aug. 11, 2016

Related U.S. Application Data

(60) Provisional application No. 62/114,778, filed on Feb. 11, 2015.

(51) Int. Cl.
*A61N 1/368* (2006.01)
*H02J 7/00* (2006.01)
(Continued)

(52) U.S. Cl.
CPC .......... *A61N 1/3684* (2013.01); *A61N 1/056* (2013.01); *A61N 1/36* (2013.01); *A61N 1/3686* (2013.01);
(Continued)

(58) Field of Classification Search
CPC .............................. A61N 1/3684; A61N 1/3686
See application file for complete search history.

(56) References Cited

U.S. PATENT DOCUMENTS 5,941,906 A 8/1999 Barreras, Sr. et al.
6,324,425 B1 * 11/2001 Blow .................. A61N 1/3627
607/13
(Continued)

FOREIGN PATENT DOCUMENTS

CN 107530546 A 1/2018
JP 2018508274 A 3/2018
WO WO-2016130654 A1 8/2016

OTHER PUBLICATIONS

"Australian Application Serial No. 2016219366, First Examination Report dated Oct. 30, 2017", 3 pgs.
(Continued)

*Primary Examiner* — Alyssa M Alter
(74) *Attorney, Agent, or Firm* — Schwegman Lundberg & Woessner, P.A.

(57) ABSTRACT

An apparatus comprises a stimulus circuit, a recharge circuit, a switch circuit, and a control circuit. The stimulus circuit provides electrical cardiac pacing stimulation to multiple combinations of a plurality of electrodes, and the electrical stimulation is selectively applied at the first electrode of the electrode combinations. The recharge circuit includes a recharge capacitor electrically coupled to the second electrode of the electrode combinations, and the switch circuit selectively enables electrode combinations for electrical coupling to the stimulus circuit and the recharge circuit. The control circuit includes a pacing activation sub-circuit that selectively initiates delivery of the electrical stimulation using multiple electrode combinations, and enables simultaneous delivery of pacing recharge energy from the recharge capacitor to the second electrode of multiple electrode combinations.

13 Claims, 10 Drawing Sheets

(51) Int. Cl.
     *A61N 1/05*     (2006.01)
     *A61N 1/36*     (2006.01)
     *H02J 7/34*     (2006.01)
     *A61N 1/365*     (2006.01)

(52) U.S. Cl.
     CPC .......... *H02J 7/007* (2013.01); *A61N 1/36521* (2013.01); *H02J 7/345* (2013.01)

(56) References Cited

U.S. PATENT DOCUMENTS

| | | |
|---|---|---|
| 2011/0276103 A1 | 11/2011 | Maile et al. |
| 2012/0116482 A1 | 5/2012 | Linder et al. |
| 2014/0107720 A1 | 4/2014 | Bornzin |
| 2014/0243924 A1 | 8/2014 | Zhu et al. |

OTHER PUBLICATIONS

"Australian Application Serial No. 2016219366, Response filed May 25, 2018 to First Examination Report dated Oct. 30, 2017", 15 pgs.

"European Application Serial No. 16708819.4, Response filed Mar. 8, 2018 to Communication Pursuant to Rules 161(1) and 162 EPC dated Sep. 19, 2017", 25 pgs.

"International Application Serial No. PCT/US2016/017321, International Preliminary Report on Patentability dated Aug. 24, 2017", 10 pgs.

"International Application Serial No. PCT/US2016/017321, International Search Report dated May 9, 2016", 6 pgs.

"International Application Serial No. PCT/US2016/017321, Written Opinion dated May 9, 2016", 8 Pgs.

\* cited by examiner

MANAGED PACE RECHARGE IN A MULTIPOINT PACING SYSTEM

CLAIM OF PRIORITY

This application claims the benefit of priority under 35 U.S.C. § 119(e) of U.S. Provisional Patent Application Ser. No. 62/114,778, filed on Feb. 11, 2015, which is herein incorporated by reference in its entirety.

BACKGROUND

Implantable medical devices (IMDs) are implantable or partially implantable. Some examples include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and may include electrodes that are able to sense cardiac signals without being in direct contact with the patient's heart. Other examples of IMDs include implantable diagnostic devices, implantable drug delivery systems, or implantable devices with neural stimulation capability (e.g., vagus nerve stimulator, baroreflex stimulator, carotid sinus stimulator, deep brain stimulator, sacral nerve stimulator, etc.).

Operation of an IMB is typically optimized for particular patient by a caregiver, such as by programming different device operating parameters or settings for example. Manufacturers of such devices continue to improve and add functionality to the devices, which can make them complicated to program. The inventors have recognized a need for improved optimization of device-based therapy.

OVERVIEW

As explained above, manufacturers of IMDs continue to improve and add functionality to the devices, which may result in complex interactive limits on programmable device parameter settings. The present subject matter relates to providing multi-site pacing therapy and minimizing the complexity of the resulting interactive parameter limits.

An apparatus example of the present subject matter includes a stimulus circuit, a recharge circuit, a switch circuit, and a control circuit. The stimulus circuit provides electrical cardiac pacing stimulation to multiple combinations of a plurality of electrodes, and the electrical stimulation is selectively applied at the first electrode of the electrode combinations. The recharge circuit includes one or more recharge capacitors electrically coupled to the second electrode of the electrode combinations, and the switch circuit selectively enables electrode combinations for electrical coupling to the stimulus circuit and the recharge circuit. The control circuit includes a pacing activation sub-circuit that selectively initiates delivery of the electrical stimulation using multiple electrode combinations, and enables simultaneous delivery of pacing recharge energy from the one or more recharge capacitors to the second electrode of multiple electrode combinations.

This simultaneous charge balancing of multiple electrode combinations can provide for improved multi-site pacing therapy, as will be discussed subsequently.

The sensing time windows for cardiac activity detection are enabled in a specified relationship to paced events to avoid misidentifying a paced cardiac depolarization as intrinsic activity. The sensing time windows may be enabled after one or both of a blanking period and a refractory period after pacing stimulation is delivered. Multi-site pacing including recharging operations may have an impact on these detection windows. The recharge portion of a pacing cycle may extend well beyond the portion of time used to deliver the multi-site pacing. This can limit the time that sensing windows can be enabled to avoid incorrectly sensing the recharge energy as intrinsic cardiac activity. Recharge energy can also cause a signal artifact on the sensing if the sensing circuits are enabled (e.g., sense amplifiers of the sensing circuit may be connected to the electrode path) before electrodes are sufficiently recharged or charge balanced. Excess charge at the electrodes can cause a voltage spike at the sensing circuits when they are connected that could be incorrectly interpreted as intrinsic cardiac activity.

By providing a simultaneous charge balancing of multiple electrode combinations, the time required to charge balance multiple electrode combinations can be reduced. This, in turn, can increase the time available for sensing cardiac activity. In addition, artifacts in the sensing time window caused by charge balancing operations can be avoided.

This section is intended to provide a brief overview of subject matter of the present patent application. It is not intended to provide an exclusive or exhaustive explanation of the invention. The detailed description is included to provide further information about the present patent application such as a discussion of the dependent clams and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
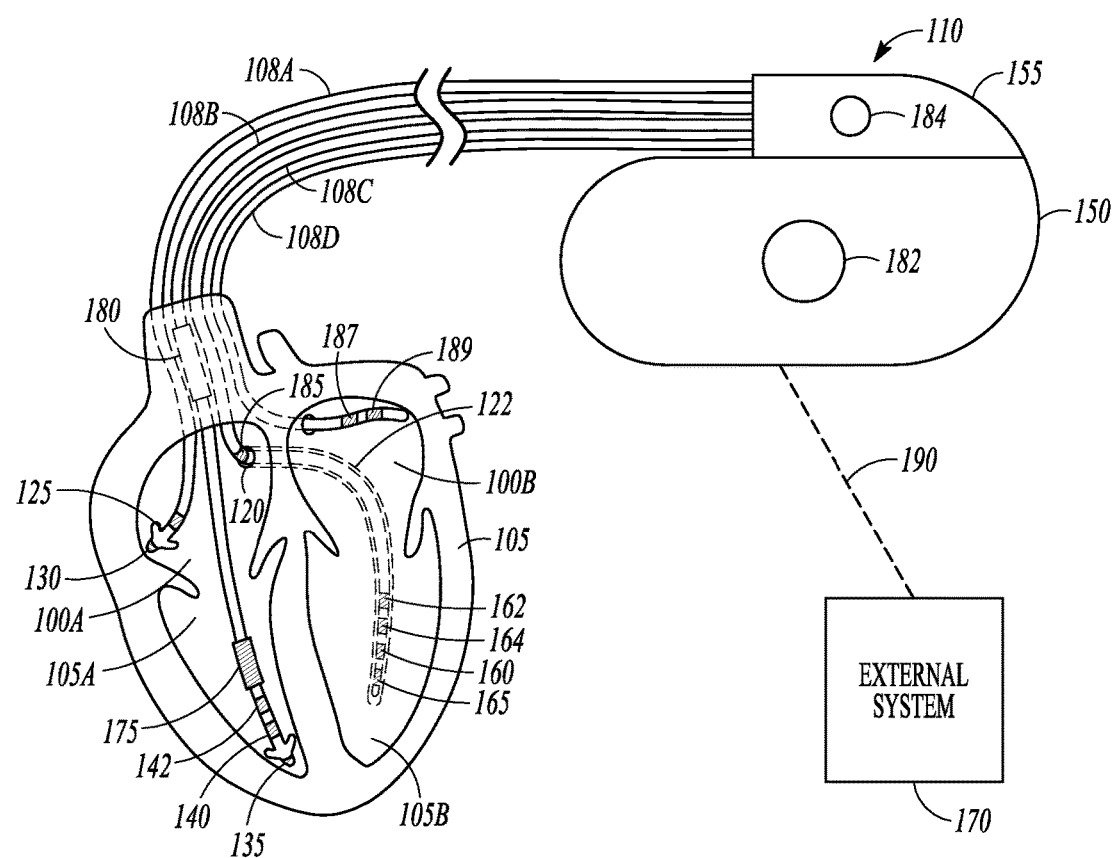
FIG. 1 is an illustration of an example of portions of a system that includes an IMD.

FIG. 1 is an illustration of portions of a system that includes an IMB 110. Examples of IMD 110 include, without limitation, a pacemaker, a defibrillator, a cardiac resynchronization therapy (CRT) device, or a combination of such devices. In other examples, the IMD is a neurostimulator such as among other things a vagus nerve stimulator, baroreflex stimulator, carotid sinus stimulator, deep brain stimulator, or sacral nerve stimulator. The system 100 also typically includes an IMD programmer or other external system 170 that communicates wireless signals 190 with the IMD 110, such as by using radio frequency (RF) or other telemetry signals.

The IMB 110 can be coupled by one or more leads 108A-D to heart 105. Cardiac leads 108A-D include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. RV lead 108B can include one or more additional ring electrodes 142 to provide multi-site pacing to the RV. Lead 108B optionally also includes additional electrodes, such as electrodes 175 and 180, for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMB 110 can include a third cardiac lead 108C attached to the IMD 110 through the header 155. The third cardiac lead 108C includes electrodes 160, 162, 164, and 165 placed in a coronary vein 122 lying epicardially on the left ventricle (LV) 105B via the coronary vein. The number of electrodes shown in the Figure is only an example and other arrangements are possible. For instance, the third cardiac lead 108C may include less electrodes (e.g., one or two electrodes) or more electrodes (e.g., eight or more electrodes) than the example shown, and may include a ring electrode 185 positioned near the coronary sinus (CS) 120.

In addition to cardiac leads 108A, 108B, 108C, or in alternative to one or more of cardiac leads 108A, 108B, 108C, the IMD 110 can include a fourth cardiac lead 108D that includes electrodes 187 and 189 placed in a vessel lying epicardially on the left atrium (LA) 100B.

The IMB 110 can include a hermetically-sealed IMD housing or can 150, and the IMB 110 can include an electrode 182 formed on the IMB can 150. The IMB header 155 may also include an electrode 184. Cardiac pacing therapy can be delivered in a unipolar mode using the electrode 182 or electrode 184 and one or more electrodes formed on a lead. Cardiac pacing therapy can be delivered in an extended bipolar pacing mode using only one electrode of a lead (e.g., only one electrode of LV lead 108C) and one electrode of a different lead (e.g., only one electrode of RV lead 108B). Cardiac pacing therapy can be delivered in a monopolar pacing mode using only one electrode of a lead without a second electrode.

Lead 108B can include a first defibrillation coil electrode 175 located proximal to tip and ring electrodes 135, 140 for placement in a right ventricle, and a second defibrillation coil electrode 180 located proximal to the first defibrillation coil electrode 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to the electrode 182 formed on the IMB can 150. This improves defibrillation by delivering current from the RV coil 175 more uniformly over the ventricular myocardium. In some examples, the therapy is delivered from the RV coil 175 only to the electrode 182 formed on the IMD can 150. In some examples, the coil electrodes 175, 180 are used in combination with other electrodes for sensing signals.

Note that the specific arrangement of leads and electrodes shown in the illustrated example of FIG. 1 is intended to be non-limiting. An IMD can be configured with a variety of electrode arrangements including transvenous, endocardial, and epicardial electrodes (e.g., an epicardial patch that may include dozens of electrodes), and/or subcutaneous, non-intrathoracic electrodes. An IMD 110 can be connectable to subcutaneous array or lead electrodes (e.g., non-intrathoracic electrodes or additional LV leads implantable along the LV wall, and leads implantable in one or both atria) that can be implanted in other areas of the body to help "steer" electrical currents produced by IMB 110. An IMB can be leadless (e.g., a leadless pacemaker). A leadless IMD may be placed in a heart chamber (e.g., RV or LV) and multiple electrodes of the leadless IMD may contact cardiac tissue. The present methods and systems will work in a variety of configurations and with a variety of electrodes.

As explained previously, functionality of implantable medical devices can make them complicated for a caregiver to program and optimize to the needs of a particular patient. For instance, a CRM device may provide multi-site pacing, in which pacing pulses are provided to multiple sites within a same heart chamber. This may be useful to improve coordination of a contraction of a heart chamber, especially of the left ventricle. In the non-limiting example shown in FIG. 1, pacing may be provided to left ventricle using LV electrodes 160 and 165 as a first bipolar electrode pair and using LV electrodes 162 and 164 as a second electrode pair in sequence to coordinate activation of different tissue sites of the left ventricle to cause contraction in a desired manner. Pacing may also be provided using RV ring electrode 140 and any of the LV electrodes as part of the activation sequence. In another example, a pace pulse may be provided to left ventricle using can electrode 182 in combination with LV electrode 165 as a first unipolar electrode pair followed by a sequence of pulses delivered using combinations of the can electrode 182 with other LV electrodes.

Electrodes used to provide electrical pacing therapy can degrade if residual charge builds up at the electrode tissue interface. Charge buildup can also increase the pacing energy needed to trigger cardiac activation. This pacing energy is sometimes called a pacing threshold. To prevent buildup of DC voltage at an electrode a blocking capacitor can be included between an electrode and circuit ground. Additionally, charge balance at electrodes can be maintained by delivering a recharge pulse from energy stored on the blocking capacitor. For this reason, the blocking capacitor can also be referred to as a recharge capacitor.

Figure 2:
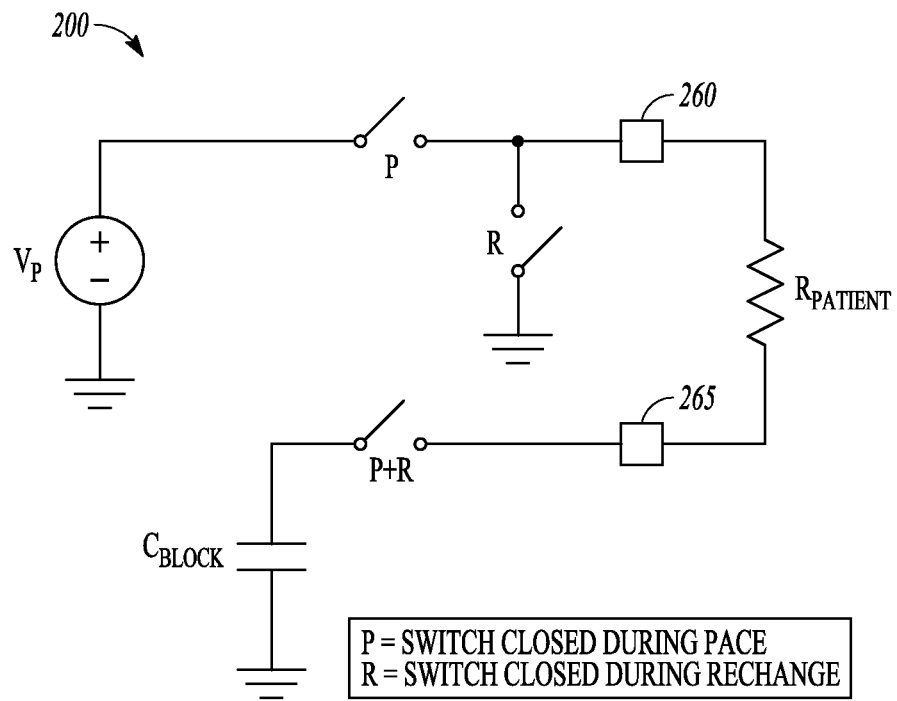
FIG. 2 illustrates an example of a recharge circuit with two electrodes.

FIG. 2 shows an example of a recharge circuit 200 where only two electrodes are used to deliver an electrical stimulation pulse. The circuit includes three switches to steer the electrical pacing stimulation energy and the pacing recharge energy. When pacing is to be delivered the pacing switch labeled P and the switch labeled P+R are activated or closed and the recharge switch labeled R is inactive or open. Energy is delivered from the pacing energy source $V_P$ (e.g., a battery or capacitor) to electrode 260 to cardiac tissue of the patient to electrode 265 to recharge capacitor or blocking capacitor $C_{BLOCK}$. For the delivery of recharge energy, the switch P is open, switch R is closed and switch P+R is closed. Pacing recharge energy stored on the blocking capacitor $C_{BLOCK}$ is delivered from the blocking capacitor to electrode 265 to the cardiac tissue of the patient to electrode 260 to system ground.

Figure 3:
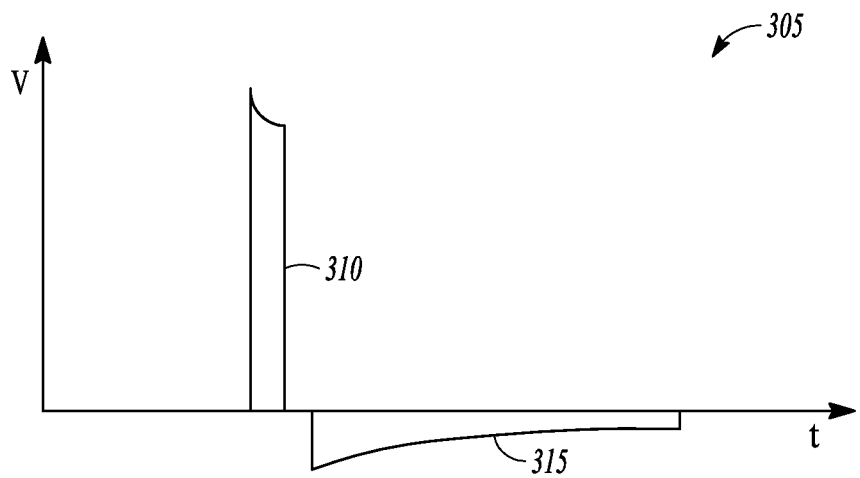
FIG. 3 shows an example of a waveform having a pacing stimulation pulse and a recharge pulse.

FIG. 3 shows an example of a waveform 305 including the pacing stimulation pulse and the recharge pulse. The waveform is biphasic and during a first phase 310 a pacing stimulation pulse is delivered from the pacing energy source. During a second phase 315, a charge-restoring pulse is delivered from a blocking capacitor or recharge capacitor to balance the charge at the electrodes. The area of the first phase 310 (e.g., amplitude×width) equals the area of the second phase 315 to maintain charge balance. The recharge phase prevents an imbalance in charge from developing at the electrodes and prevents change to the pacing threshold and degradation of the electrodes. The example of FIG. 3 shows the pace pulse as a positive pulse and the recharge pulse as a negative pulse, but in variations the polarities can be reversed. The recharge circuit shown in the example is a passive circuit because charge from the electrical cardiac pacing stimulation therapy is reserved using the recharge capacitor and used as the recharge energy. An example of an active recharge circuit delivers a pulse similar to the pacing pulse but with reversed polarity. An advantage of passive recharge versus active recharge is that passive recharge consumes less battery energy.

Multi-site pacing can complicate the pace-recharge cycle of pacing therapy. The additional pacing sites impact the amount of time needed to recharge all of the pacing sites if the approach to delivery recharge previously described is merely duplicated for each pacing site. An advantage of active recharge to passive recharge in a multi-site pacing application is that active recharge is faster than passive recharge because the passive recharge pulse may be longer to allow the reserved recharge energy to dissipate from the capacitor. The methods and devices described herein will work both passive recharge and active recharge.

Figure 4:
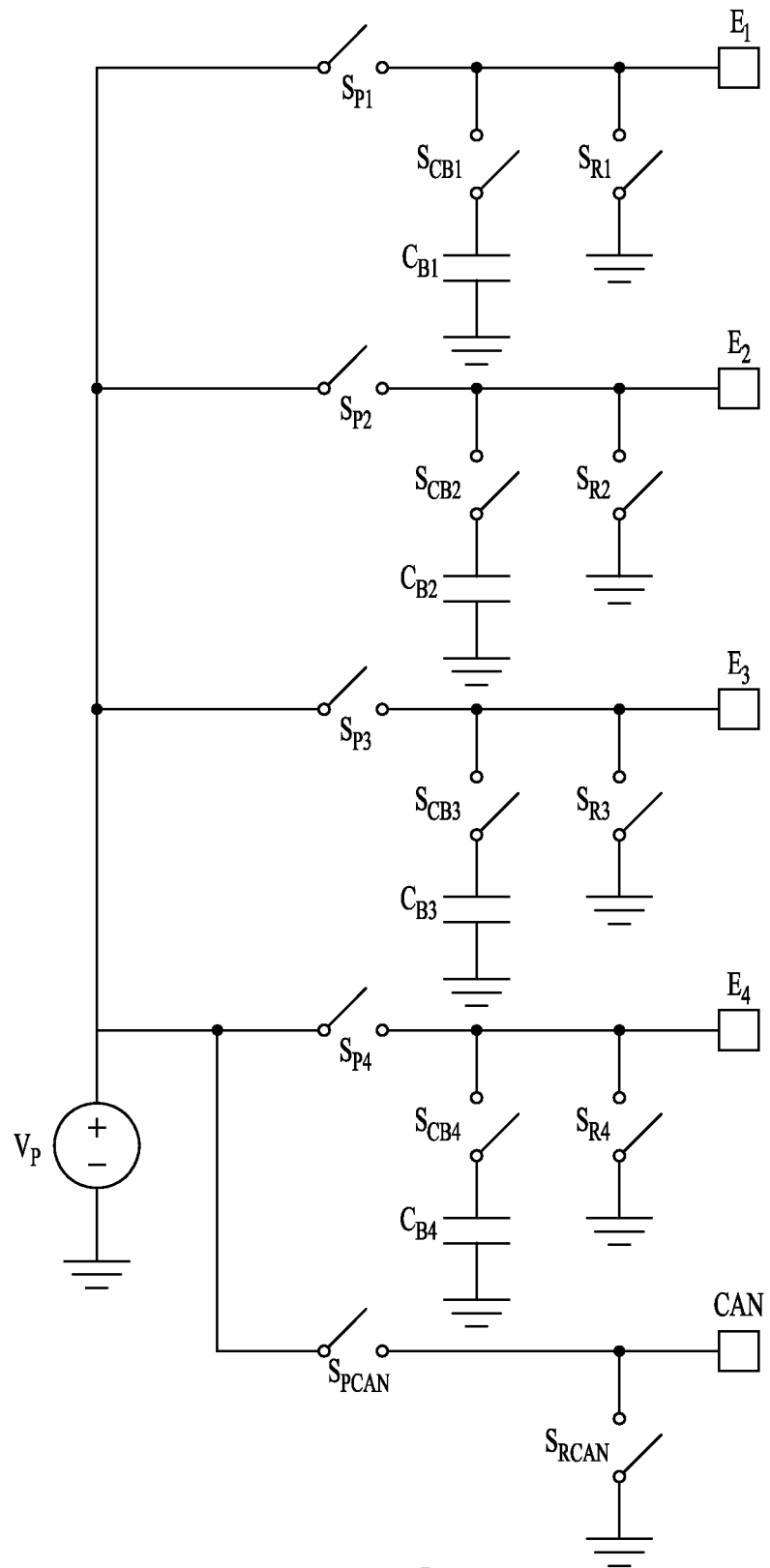
FIG. 4 shows an example of a circuit diagram in which multiple electrodes are used to provide multi-site pacing.

FIG. 4 shows an example of a circuit diagram 400 in which multiple electrodes are used to provide multi-site pacing and recharge. Electrodes labeled $E_1$-$E_4$ may correspond to electrodes 160, 162, 164, and 165 in the example of FIG. 1 and the electrode labeled Can may correspond to electrode 182 in FIG. 1. To provide bipolar pacing using electrodes $E_1$ and $E_2$, the pace switch labeled $S_{P1}$ is active, the switches labeled $S_{CB1}$ and $S_{R1}$ are inactive, the switches labeled $S_{P2}$ and $S_{R2}$ are inactive, and the switch labeled $S_{CB2}$ is active. In the pacing phase, pacing stimulation energy is delivered from electrode $E_1$ to electrode $E_2$ and the stimulation energy is reserved on blocking cap $C_{B2}$. In certain examples, electrode $E_1$ is the pacing anode and electrode $E_2$ is the pacing cathode. During the recharge phase, switches $S_{CB2}$ and $S_{R1}$ are active and switches $S_{P1}$, $S_{CB1}$, $S_{P2}$, and $S_{R2}$ are inactive. Pacing recharge energy is delivered from electrode $E_2$ to $E_1$ from capacitor $C_{B2}$.

The bipolar pacing using electrodes $E_1$ and $E_2$ may be followed as part of a sequence of multi-site pacing with bipolar pacing using electrodes $E_3$ and $E_4$. If the pace-recharge scheme of the example of FIG. 2 is used, the bipolar pacing with $E_3$ and $E_4$ may not be able to be delivered at the desired time relative to the bipolar pacing with electrodes $E_1$ and $E_2$. The pace-recharge scheme of FIG. 2 can be improved, but any new scheme should not add new complexity to interactive limits of device operating parameters.

Figure 5:
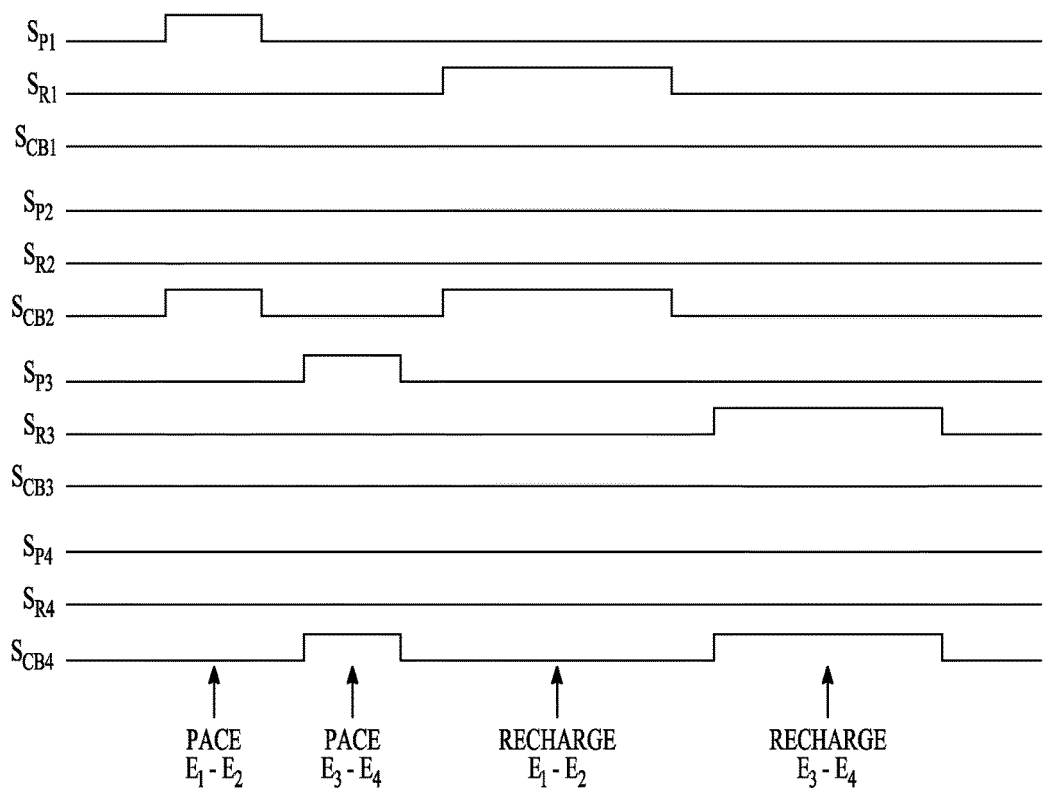
FIG. 5 shows a timing diagram of an example operation of the circuit example of FIG. 4.

FIG. 5 shows a timing diagram of an example operation of the circuit example of FIG. 4. In the example, the pacing stimulation pulse delivered using bipolar electrode pair $E_1$, $E_2$ and the pacing stimulation pulse delivered using bipolar electrode pair $E_3$, $E_4$ are delivered before the recharge energy is delivered using $E_1$, $E_2$. This allows the multi-site pacing to be delivered to the subject with the desired timing relationship between pacing pulses and still provide recharge energy to the electrodes.

Electrodes $E_1$-$E_4$ may also be used to sense intrinsic electrical cardiac activity. Electrodes can be used to sense intrinsic depolarization to trigger electrical pacing therapy and to sense cardiac tachyarrhythmia which may trigger delivery of anti-tachyarrhythmia therapy. Sensing time windows for cardiac activity detection are enabled in a specified relationship to paced events to avoid misidentifying a paced cardiac depolarization as intrinsic activity. The sensing time windows may be enabled after one or both of a blanking period and a refractory period after pacing stimulation is delivered.

Multi-site pacing may have an impact on these detection windows. In the pacing recharge scheme of FIG. 5, the recharge portion of the cycle extends well beyond the portion of time used to deliver the multi-site pacing. This can limit the time that sensing windows can be enabled to avoid incorrectly sensing the recharge energy as intrinsic cardiac activity. Recharge energy can also cause a signal artifact on the sensing if the sensing circuits are enabled (e.g., sense amplifiers of the sensing circuit may be connected to the electrode path) before electrodes are sufficiently recharged or charge balanced. Excess charge at the electrodes can cause a voltage spike at the sensing circuits when they are connected that could be incorrectly interpreted as intrinsic cardiac activity.

Figure 6:
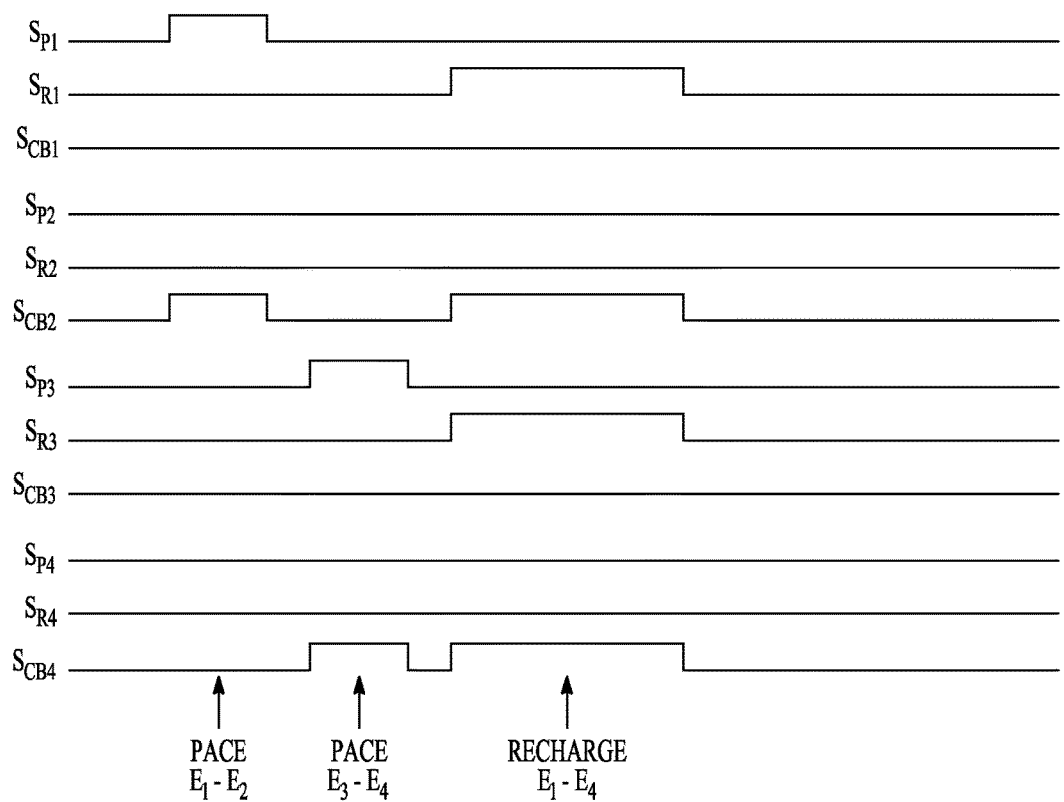
FIG. 6 shows a timing diagram of another example operation of the circuit example of FIG. 4.

FIG. 6 shows a timing diagram of another example operation of the circuit example of FIG. 4. The difference from the example of FIG. 5 is that recharge energy is delivered to all of the electrodes at the same time following the completion of delivering the sequential pacing stimuli. This approach takes advantage of the electrodes being in close physical proximity (e.g., electrodes $E_1$-$E_4$ all being positioned on the LV free wall) to simultaneously charge balance the electrodes.

Figure 7:
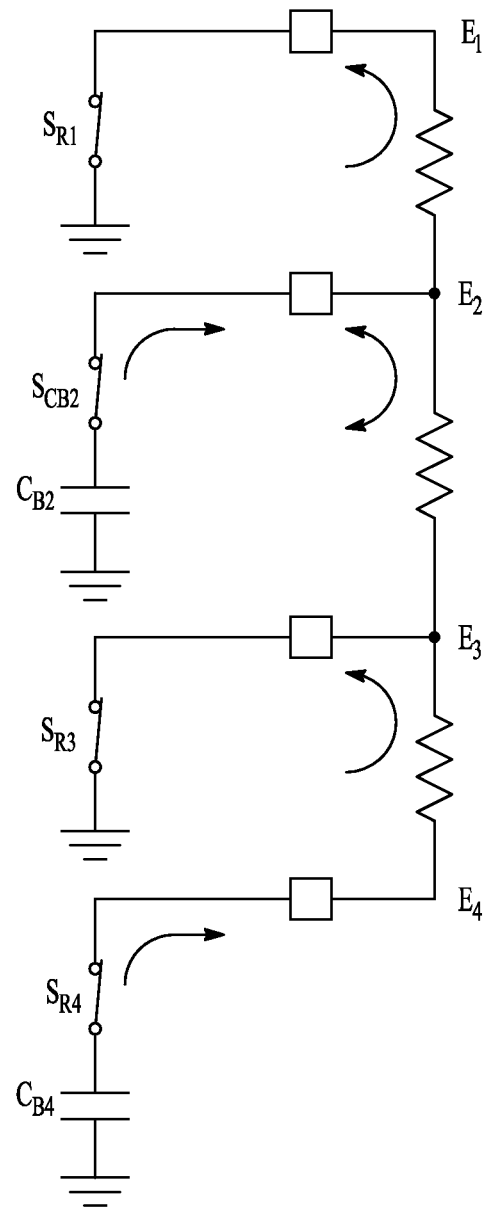
FIG. 7 shows an example of an equivalent circuit diagram in which all of the recharge circuits are activated at the same time following sequential pacing stimulation.

FIG. 7 shows an example of an equivalent circuit when all of the recharge circuits are activated at the same time following the sequential bipolar stimulation of FIG. 6. The example shows that there can be multiple paths for the recharge energy to follow. If the electrodes are in close physical proximity, residual charge on the electrodes from the pacing energy can be removed.

Figure 8:
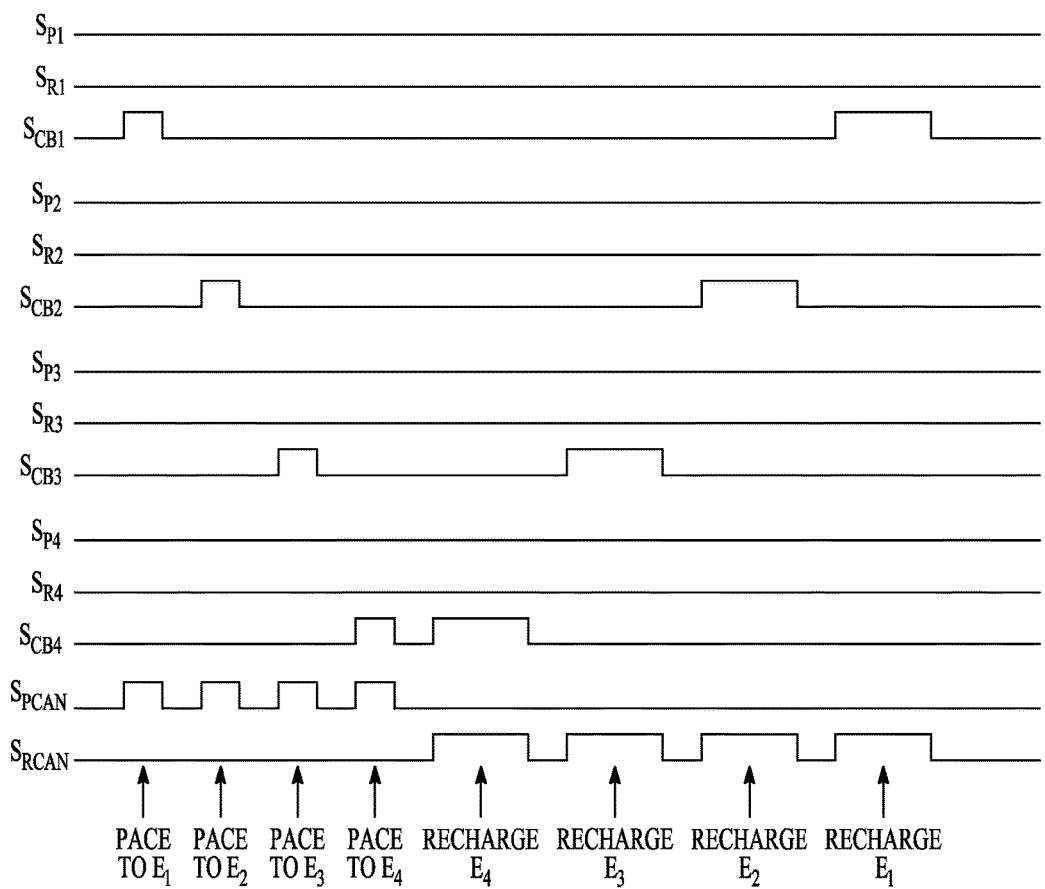
FIG. 8 shows a timing diagram of another example operation of the circuit example of FIG. 4.

FIG. 8 shows a timing diagram of another example operation of the circuit example of FIG. 4. In the example, pacing stimulation pulses are delivered in a unipolar mode. To provide unipolar pacing using the electrode labeled Can and the electrode labeled $E_1$, switches $S_{PCAN}$ and $S_{CB1}$ are active and switches $S_{RCAN}$, $S_{R1}$ and $S_{P1}$ are inactive during the pacing phase. In certain examples, the electrode labeled Can is the pacing anode and electrode $E_1$ is the pacing cathode. In the recharge phase, switches $S_{CB1}$ and $S_{RCAN}$ are active, and switches $S_{P1}$, $S_{R1}$, and $S_{PCAN}$ are inactive. In the example of FIG. 8, all of the pacing pulses are delivered sequentially using electrodes Can and $E_1$-$E_4$ before the recharge energy is delivered to the electrodes. The example shows that there can be a significant delay before sensing windows can be enabled.

Figure 9:
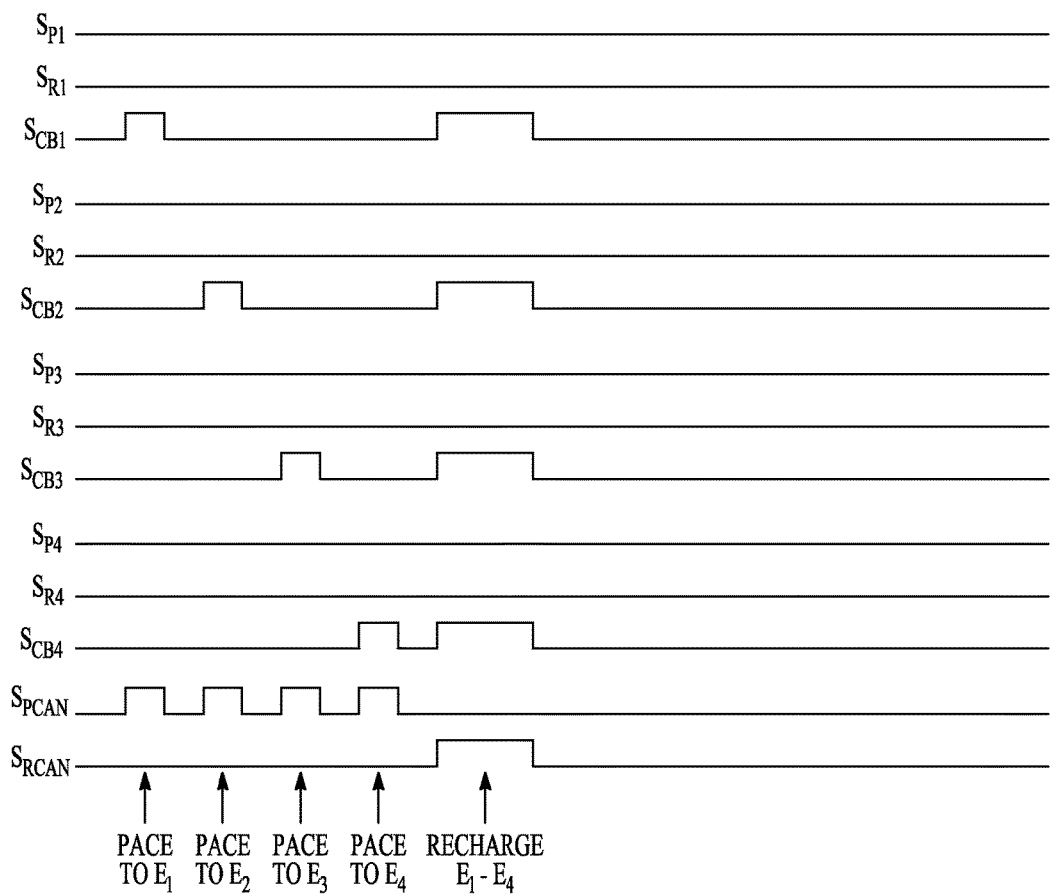
FIG. 9 shows a timing diagram of still another example operation of the circuit example of FIG. 4.

FIG. 9 shows a timing diagram of another example operation of the circuit example of FIG. 4. In the example, recharge energy is delivered to all of the electrodes at the same time (or at nearly the same time with at least some overlap in the delivery of the recharge energy to the electrodes) in the following the completion of delivering the sequential unipolar pacing stimuli, and the recharge cycles to balance the charge at the electrodes coincide and occur simultaneously or substantially simultaneously. Although the examples in FIGS. 4-8 refer to LV electrodes such as electrode 160, 162, 164, and 165 in FIG. 1, and refer to a Can electrode such as electrode 182 in FIG. 1, the methods can be applied to other combinations of electrodes such as other combinations of the electrodes shown in FIG. 1.

Figure 10:
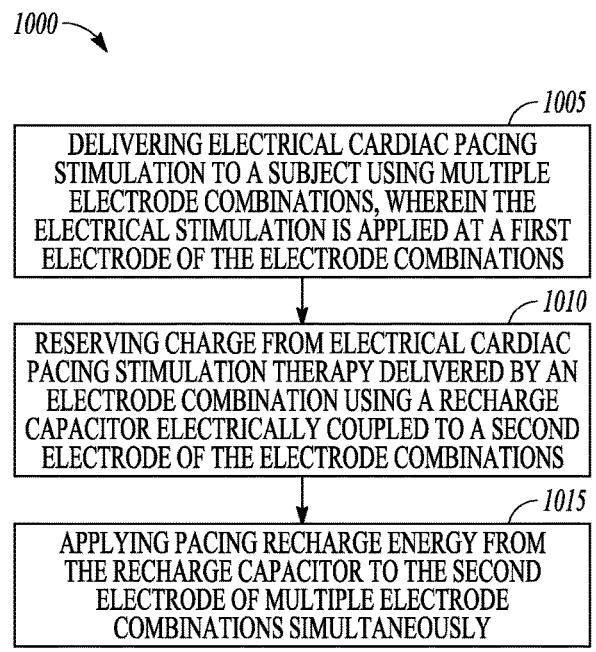
FIG. 10 is a flow diagram of a method of controlling operation of an IMB.

FIG. 10 is a flow diagram of a method 1000 of controlling operation of a pre-deployed IMB. At 1005, electrical cardiac pacing stimulation is delivered to a subject using multiple electrode combinations. The electrode combinations include at least a first electrode and a second electrode. The electrode combinations can be enabled independently and electrical stimulation is selectively applied at the first electrode of the electrode combinations. In certain examples, the first electrode operates as a cathode for the electrode combinations.

At 1010, charge from electrical cardiac pacing stimulation therapy delivered by an electrode combination is reserved using a recharge capacitor electrically coupled to the second electrode of the electrode combinations. In certain examples, the second electrode operates as the cathode for the electrode combination. In variations, the electrode combinations can include more than two electrodes, such as three electrodes in a tripolar electrode arrangement. For instance, a combination of electrodes can include the electrode labeled Can as the anode and electrodes $E_1$ and $E_2$ electrically coupled together as the cathode.

At 1015, pacing recharge energy from the recharge capacitor is applied to the second electrode of multiple electrode combinations simultaneously. The recharge operation is passive because the recharge energy is reserved from the pacing stimulation energy.

Figure 11:
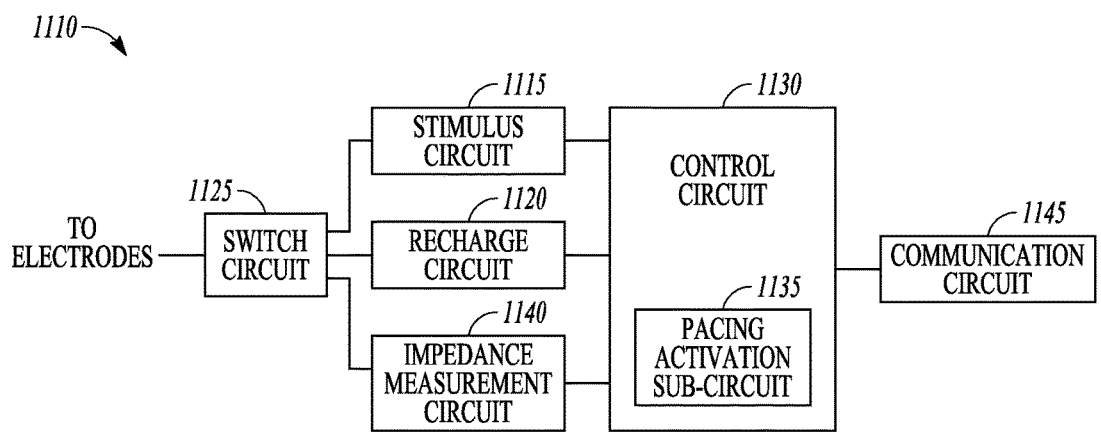
FIG. 11 shows a block diagram of portions of an example of an IMD.

FIG. 11 shows a block diagram of portions of an example of an IMD 1110. The IMD 1110 can be electrically coupled to a plurality of electrodes implantable at a plurality of tissue sites of a heart chamber of a subject. In certain examples, the electrodes are implantable at a plurality of tissue sites of a left ventricle and at least one tissue site of a right ventricle of a subject. The example of FIG. 1 shows some possible arrangements of the electrodes.

Returning to FIG. 11, the IMD 1110 includes a stimulus circuit 1115 that provides electrical cardiac pacing stimulation to multiple combinations of the plurality of electrodes. An electrode combination includes at least a first electrode and a second electrode and the electrical stimulation is selectively applied at the first electrode of the electrode combinations. An electrode combination can include a bipolar electrode pair such as LV electrodes 165 and 160 in FIG. 1 with electrode 165 as the anode. In certain examples, the IMD 1110 of FIG. 11 is electrically coupled to an implantable cardiac lead incorporating at least a portion of the plurality of electrodes. The passive recharge circuit 1120 provides recharge energy to at least one combination of electrodes that includes the bipolar electrode pair.

The IMD 1110 can include a hermetically sealed housing, a can electrode incorporated into the hermetically sealed housing, and an implantable cardiac lead incorporating at least a portion of the plurality of electrodes. In certain examples, an electrode combination can include a unipolar electrode pair such as electrode 182 formed on the IMD housing and LV electrode 162 as shown in FIG. 1; with electrode 182 as the anode. The passive recharge circuit 1120 provides recharge energy to at least one combination of electrodes that includes the can electrode and at least one electrode incorporated into the cardiac lead. In certain examples, an electrode combination can include more than two electrodes such as the tripolar electrode combination described previously herein. In certain examples, the IMD 1110 is leadless.

Returning to FIG. 11, the IMD 1110 includes a passive recharge circuit 1120 including one or more recharge capacitors or blocking capacitors (e.g., multiple recharge capacitors or blocking capacitors) electrically coupled to the second electrode of the electrode combinations. One or both of the first electrode and the second electrode can be included in a compound electrode consisting of two or more electrodes electrically coupled together. The IMD 1110 includes a switch circuit 1125 that selectively enables electrode combinations for electrical coupling to the stimulus circuit 1115 and the passive recharge circuit 1120. This can make the enabling of an electrode combination independent from the enabling of other electrode combinations for delivery of pacing stimulation energy or recharge energy.

The IMD 1110 also includes a control circuit 1130. The control circuit 1130 can include can include a microprocessor, a digital signal processor, application specific integrated circuit (ASIC), or other type of processor, interpreting or executing instructions included in software or firmware. The control circuit 1130 can include sub-circuits to perform the functions described. These sub-circuits may include software, hardware, firmware or any combination thereof. Multiple functions can be performed in one or more of the sub-circuits as desired.

The control circuit 1130 includes a pacing activation sub-circuit 1135 that selectively initiates delivery of the electrical stimulation using multiple electrode combinations, and enables simultaneous delivery of pacing recharge energy from a recharge capacitor to a second electrode of multiple electrode combinations. In some examples, the pacing activation sub-circuit 1135 initiates sequential delivery of electrical stimulation pulses to the multiple electrode combinations. For instance, stimulation pulses may be sequentially applied to multiple electrodes arranged in the left ventricle. In certain variations the pacing activation sub-circuit 1135 may initiate delivery of pacing recharge energy from all of the recharge capacitors simultaneously to all of the second electrodes of the multiple electrode combinations.

In certain variations, the pacing activation sub-circuit 1135 may initiate delivery of pacing recharge energy to the electrodes of multiple electrode combinations, but not all of the multiple electrode combinations at the same time. The pacing activation sub-circuit 1135 can initiate delivery of multiple sequential electrical stimulation pulses using a first subset of multiple electrode combinations of the plurality of electrodes, and initiate simultaneous delivery of pacing recharge energy associated with the delivery of electrical stimulation pulses by the first subset of multiple electrode combinations. The pacing activation sub-circuit 1135 may then initiate delivery of multiple sequential electrical stimulation pulses using a second subset of multiple electrode combinations of the plurality of electrodes, and initiate simultaneous delivery of pacing recharge energy associated with the delivery of electrical stimulation pulses by the second subset of multiple electrode combinations. The delivery of energy to the second subset may complete the pacing cycle, or the pacing cycle may continue with delivery of pacing and recharge energy to a third of multiple electrode combinations.

In some examples, the control circuit 1130 determines a pacing stimulation interval. The pacing stimulation interval may be specified through programming of the device, or the pacing stimulation interval may be determined according to the output received from a sensor circuit. For instance, the control circuit 1130 may adjust the pacing stimulation interval according to the output from a patient activity sensor. The control circuit 1130 may selectively enable simultaneous delivery of the pacing recharge energy according to the determined pacing stimulation interval. In certain examples, the control circuit 1130 changes the recharge capacitors used to simultaneously deliver the pacing recharge energy according to the determined pacing stimulation interval. For instance, the control circuit 1130 may add simultaneous delivery of recharge energy to some and eventually to all electrode combinations as the pacing stimulation interval is decreased as heart rate increases. This may be useful to increase the time available for sensing windows to operate.

According to some examples, the pacing activation sub-circuit 1135 initiates delivery of a first electrical stimulation pulse having a first pulse amplitude to a first electrode combination, and initiates sequential delivery of a second electrical stimulation pulse having a second pulse amplitude to a second electrode combination. If the difference between the amplitudes of the two stimulation pulses is too great, simultaneously applying recharge energy from the delivered pacing stimuli may result in a charge imbalance at the electrode cardiac tissue interface. A charge imbalance great enough may cause unwanted cardiac capture. The control circuit 1130 may disable the simultaneous delivery of pacing recharge energy when the second pulse amplitude differs from the first pulse amplitude by a specified threshold pulse amplitude difference value. In certain variations, the simultaneous delivery of recharge energy is disabled when the amplitude of the second stimulation pulse amplitude is more than three times the amplitude of the first stimulation pulse. In certain variations, the simultaneous delivery of recharge energy is disabled when the amplitude of the second stimulation pulse amplitude is more than four times the amplitude of the first stimulation pulse. Pulse amplitude can refer to voltage amplitude as shown in FIG. 3 or current amplitude with the vertical axis in FIG. 3 being current (e.g., microamps) instead of voltage.

In some examples, the control circuit 1130 enables or disables the simultaneous delivery of recharge energy according to a combination of pulse width and pulse amplitude. The product of current/and pulse width PW (e.g., I*PW) can correspond to charge (e.g., coulombs) delivered to an electrode combination. The control circuit 1130 may disable the simultaneous delivery of recharge energy when charge delivered to a first electrode combination differs from the charge delivered to a second electrode combination by a specified threshold charge difference value.

For instance, the pacing activation sub-circuit 1135 may initiate delivery of a first electrical stimulation pulse having a first current amplitude $I_1$ and pulse width $PW_1$ to a first electrode combination, and initiate sequential delivery of a second electrical stimulation pulse having a second current amplitude $I_2$ and pulse width $PW_2$ to a second electrode combination. The control circuit 1130 may determine a ratio of the products of the amplitude and pulse width (e.g., ratio=$I_1*PW_1/I_2*PW_2$) and enable or disable the simultaneous delivery of pacing recharge energy when the ratio satisfies a specified threshold ratio value.

This gating or enabling of simultaneous recharge can correspond to recharge modes. For example, the pacing activation sub-circuit 1135 may initiate delivery of a first electrical stimulation pulse having a first pulse amplitude to a first electrode combination, and initiate sequential delivery of a second electrical stimulation pulse having a second pulse amplitude to a second electrode combination. When the second pulse amplitude differs from the first pulse amplitude by less than a specified threshold pulse amplitude difference value, recharge energy is delivered in a first recharge mode in which the pacing activation sub-circuit 1135 initiates delivery of the first recharge energy pulse and the second recharge energy pulse simultaneously after the second electrical stimulation pulse. When the second pulse amplitude differs from the first pulse amplitude by at least the specified threshold pulse amplitude difference value, recharge energy is delivered in a second recharge mode in which a first recharge energy pulse to the first electrode combination after the first electrical stimulation pulse, and deliver a second recharge energy pulse to the second electrode combination after the second electrical stimulation pulse.

Applying recharge energy simultaneously to multiple electrodes can be complicated by large impedance imbalances among the multiple electrode combinations used to deliver pacing stimulation. Referring to the example of FIG. 7 in which all of the recharge circuits are simultaneously activated at the same time, large impedance imbalances between electrodes may cause recharge energy to take different paths than intended. This may be a particular concern for unipolar pacing configurations and may lead to transient currents that may cause unwanted cardiac capture.

In some examples, simultaneous delivery of recharge energy can be enabled according to device determined impedance. The IMD 1110 may include an impedance measurement circuit 1140 electrically coupled to the switch circuit 1125. The impedance measurement circuit 1140 generates an impedance signal representative of the impedance of an electrode combination.

In some variations, the impedance signal includes a voltage proportional to the impedance of an electrode combination. The impedance can be measured by applying a specified non-stimulating excitation current pulse across the load, such as between electrodes 182 and 162 in FIG. 1. The excitation current is non-stimulating because it has an amplitude lower than the minimum amplitude for pacing stimulation (i.e., it has low enough amplitude that it does not trigger a heart depolarization or stimulate a nerve), or it has a pulse width narrower than a minimum pulse width for pacing stimulation. The resulting voltage between the electrodes is then measured. The measured voltage may be divided by the excitation current to obtain a resistance value. Examples of systems and methods of measurement of lead impedance are found in Linder et al., U.S. Pat. No. 6,317,628, "Cardiac Rhythm Management System with Painless Defibrillation Lead Impedance Measurement," filed Jan. 25, 1999, which is incorporated herein in its entirety.

The control circuit 1130 initiates a measurement of a first impedance of a first electrode combination and initiates a measurement of a second impedance of a second electrode combination. The control circuit 1130 disables the simultaneous delivery of pacing recharge energy when the first impedance differs from the second impedance by a specified threshold impedance difference value. In certain variations, the control circuit 1130 disables the simultaneous delivery of pacing recharge energy when the measured value of the second impedance is three times the measured value of the first impedance. In certain variations, the control circuit 1130 disables the simultaneous delivery of pacing recharge energy when the second impedance is four times the first impedance.

According to some examples, simultaneous delivery of recharge energy can be enabled according to the electrode configuration coupled to the IMD 1110. The electrode configuration may include combinations of electrodes in close enough physical proximity to take advantage of the simultaneous delivery. The control circuit 1130 may determine the electrode arrangement electrically coupled to the IMD 1110 and enable the simultaneous delivery of pacing recharge energy from the recharge capacitors according to the determined electrode arrangement. In certain examples, the control circuit 1130 determines the electrode configuration by detecting that a specified type of cardiac lead is coupled to the IMD 1110, such as cardiac lead 108C of the example of FIG. 1. In certain examples, the control circuit 1130 initiates impedance measurements among electrodes and enables simultaneous delivery of recharge energy when the inter-electrode impedances are below a specified threshold impedance value.

In some examples, the IMD 1110 includes a communication circuit 1145 electrically coupled to the control circuit 1130. The communication circuit 1145 receives an indication of the electrode arrangement electrically coupled to the IMD from a separate device, such as external system 170 in the example if FIG. 1. The control circuit 1130 enables the simultaneous delivery of pacing recharge energy from the recharge capacitors according to the indicated electrode arrangement. In certain examples, the indication of the electrode arrangement includes an indication that the IMD 110 is coupled to multiple electrodes that are arranged in a single heart chamber.

Figure 12:
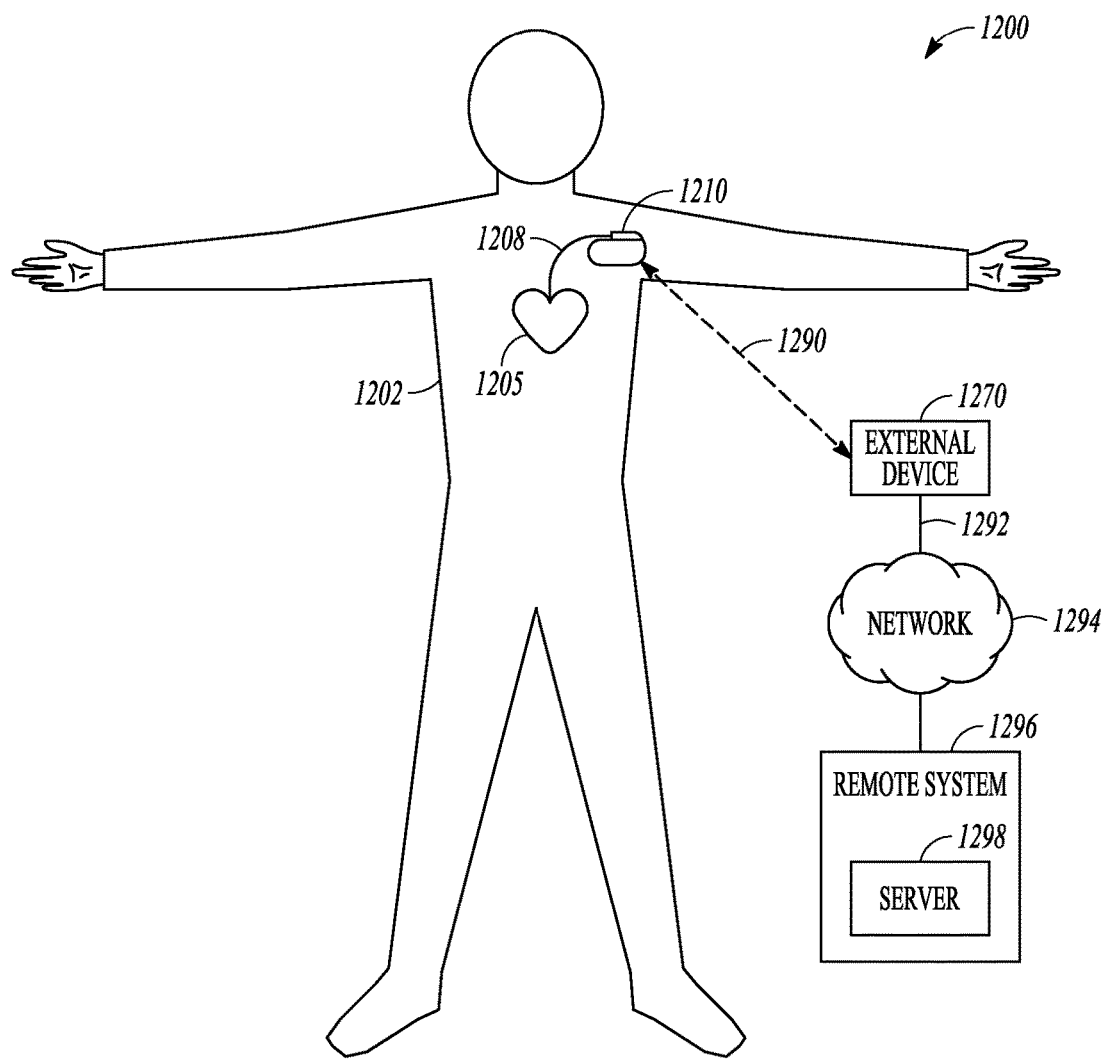
FIG. 12 is an illustration of portions of another example of a system that uses a deployed IMD.

FIG. 12 is an illustration of portions of an example of a system 1200 that uses a deployed IMD 1210 to provide a therapy to a patient 1202. The system 1200 typically includes an external device 1270 that communicates with a remote system 1296 via a network 1294. The network 1294 can be a communication network such as a cellular phone network or a computer network (e.g., the internet). In some examples, the external device 1270 includes a repeater and communicated via the network using a link 1292 that may be wired or wireless. In some examples, the remote system 1296 provides patient management functions and may include one or more servers 1298 to perform the functions. In some examples, the remote system 1296 provides electrode activation information for use with the methods of multi-site pacing and simultaneous delivery of recharge energy described previously. For instance, the remote system 1296 may provide heart rate limits or thresholds at which simultaneous delivery of recharge energy can be activated and deactivated. In another example, the remote system 1296 may provide electrode configuration information to the IMD 1210 to determine activation/deactivation of the simultaneous delivery of recharge energy.

The devices and methods described herein allow for multi-site pacing to be delivered to the subject with the desired timing relationship between pacing pulses and still provide recharge energy to the electrodes to avoid degrading of the electrodes and avoid increases in the pacing threshold. The improved recharge energy delivery does not add complex interactive limits of device operating parameters that need to be learned by a clinician or caregiver.

ADDITIONAL NOTES AND EXAMPLES

Example 1 can include subject matter (such as an apparatus for coupling to a plurality of electrodes) comprising a stimulus circuit, a recharge circuit, a switch circuit and a control circuit. The stimulus circuit is optionally configured to provide electrical cardiac pacing stimulation to multiple combinations of the plurality of electrodes, wherein an electrode combination includes at least a first electrode and a second electrode and the electrical stimulation is selectively applied at the first electrode of the electrode combinations. The recharge circuit optionally includes one or more recharge capacitors electrically coupled to the second electrode of the electrode combinations. The switch circuit is optionally configured to selectively enable electrode combinations for electrical coupling to the stimulus circuit and the recharge circuit. The control circuit optionally includes a control circuit including a pacing activation sub-circuit configured to: selectively initiate delivery of the electrical stimulation using multiple electrode combinations; and enable simultaneous delivery of pacing recharge energy from the one or more recharge capacitors to the second electrode of multiple electrode combinations.

In Example 2, the subject matter of Example 1 optionally includes multiple recharge capacitors and a pacing activation sub-circuit configured to initiate sequential delivery of electrical stimulation pulses to the multiple electrode combinations, and initiate delivery of pacing recharge energy from all of the multiple recharge capacitors simultaneously to all of the second electrodes of the multiple electrode combinations.

In Example 3, the subject matter of Example 1 or Example 2 optionally includes a control circuit configured to determine a pacing stimulation interval and selectively change the number of recharge capacitors used to simultaneously deliver the pacing recharge energy according to the determined pacing stimulation interval.

In Example 4, the subject matter of one or any combination of Examples 1-3 optionally includes a control circuit configured to determine a pacing stimulation interval and selectively enable simultaneous delivery of the pacing recharge energy according to the determined pacing stimulation interval.

In Example 5, the subject matter of one or any combination of Examples 1-4 optionally includes a pacing activation sub-circuit configured to: initiate delivery of a first electrical stimulation pulse having a first pulse amplitude to a first electrode combination; and initiate sequential delivery of a second electrical stimulation pulse having a second pulse amplitude to a second electrode combination; and wherein the control circuit is configured to disable the simultaneous delivery of pacing recharge energy when the second pulse amplitude differs from the first pulse amplitude by a specified threshold pulse amplitude difference value.

In Example 6, the subject matter of one or any combination of Examples 1-5 optionally includes a pacing activation sub-circuit configured to: initiate delivery of a first electrical stimulation pulse having a first pulse amplitude and a first pulse width to a first electrode combination; and initiate sequential delivery of a second electrical stimulation pulse having a second pulse amplitude and a second pulse width to a second electrode combination; and wherein the control circuit is configured to determine charge applied to the electrode combinations and disable the simultaneous delivery of pacing recharge energy when charge applied to the second electrode combination differs from the charge applied to the first electrode combination by a specified threshold charge difference value.

In Example 7, the subject matter of one or any combination of Examples 1-6 optionally includes a pacing activation sub-circuit configured to: initiate delivery of a first electrical stimulation pulse having a first pulse amplitude to a first electrode combination; initiate sequential delivery of a second electrical stimulation pulse having a second pulse amplitude to a second electrode combination; initiate delivery, in a first recharge mode, of the first recharge energy pulse and the second recharge energy pulse simultaneously after the second electrical stimulation pulse when the second pulse amplitude differs from the first pulse amplitude by less than a specified threshold pulse amplitude difference value; and initiate delivery, in a second recharge mode, of a first recharge energy pulse to the first electrode combination after the first electrical stimulation pulse, and deliver a second recharge energy pulse to the second electrode combination after the second electrical stimulation pulse when the second pulse amplitude differs from the first pulse amplitude by at least the specified threshold pulse amplitude difference value.

In Example 8, the subject matter of one or any combination of Examples 1-7 optionally includes an impedance measurement circuit electrically coupled to the switch circuit and configured to generate an impedance signal representative of the impedance of an electrode combination, wherein the control circuit is optionally configured to initiate a measurement of a first impedance of a first electrode combination; initiate a measurement of a second impedance of a second electrode combination; and disable the simultaneous delivery of pacing recharge energy when the first impedance differs from the second impedance by a specified threshold impedance difference value.

In Example 9, the subject matter of one or any combination of Examples 1-8 optionally includes a pacing activation sub-circuit configured to: initiate delivery of multiple sequential electrical stimulation pulses using a first subset of multiple electrode combinations of the plurality of electrodes; initiate simultaneous delivery of pacing recharge energy associated with the delivery of electrical stimulation pulses by the first subset of multiple electrode combinations; initiate delivery of multiple sequential electrical stimulation pulses using a second subset of multiple electrode combinations of the plurality of electrodes; and initiate simultaneous delivery of pacing recharge energy associated with the delivery of electrical stimulation pulses by the second subset of multiple electrode combinations.

In Example 10, the subject matter of one or any combination of Example 1-9 optionally includes a control circuit configured to: determine an electrode arrangement electrically coupled to the implantable medical device; and enable the simultaneous delivery of pacing recharge energy from the recharge capacitors according to the determined electrode arrangement.

In Example 11, the subject matter of one or any combination of Examples 1-10 optionally includes a communication circuit electrically coupled to the control circuit and configured to receive an indication of an electrode arrangement electrically coupled to the implantable medical device, wherein the control circuit is optionally configured to enable the simultaneous delivery of pacing recharge energy from the recharge capacitors according to the indicated electrode arrangement.

In Example 12, the subject matter of one or any combination of Examples 1-11 optionally includes an implantable cardiac lead incorporating at least a portion of the plurality of electrodes, wherein the recharge circuit is optionally configured to provide recharge energy to at least one combination of electrodes that includes a bipolar electrode pair.

In Example 13, the subject matter of one or any combination of Examples 1-12 optionally includes a hermetically sealed housing; a can electrode incorporated into the hermetically sealed housing; and an implantable cardiac lead incorporating at least a portion of the plurality of electrodes, wherein the recharge circuit is optionally configured to provide recharge energy to at least one combination of electrodes that includes the can electrode and at least one electrode incorporated into the cardiac lead.

Example 14 can include subject matter (such as a method, a means for performing acts, or a device-readable medium including instructions that, when performed by the device, cause the device to perform acts), or can optionally be combined with the subject matter of one or any combination of Examples 1-13 to include such subject matter, comprising: delivering electrical cardiac pacing stimulation to a subject using multiple electrode combinations that include at least a first electrode and a second electrode, wherein the electrical stimulation is selectively applied at the first electrode of the electrode combinations; reserving charge from electrical cardiac pacing stimulation therapy delivered by an electrode combination using a recharge capacitor electrically coupled to the second electrode of the electrode combinations; and applying pacing recharge energy from the recharge capacitor to the second electrode of multiple electrode combinations simultaneously.

In Example 15, the subject matter of Example 14 optionally includes sequentially delivering the electrical cardiac pacing energy to the multiple electrode combinations, and wherein applying pacing recharge energy from the recharge capacitor includes applying pacing recharge energy from all of the recharge capacitors simultaneously to all of the second electrodes of the multiple electrode combinations.

In Example 16, the subject matter of Example 14 or Example 15 optionally includes selectively changing the number of recharge capacitors used to simultaneously apply the recharge energy according to a pacing stimulation interval.

In Example 17, the subject matter of one or any combination of Examples 14-16 optionally includes delivering a first electrical stimulation pulse having a first pulse amplitude to a first electrode combination; sequentially delivering a second electrical stimulation pulse having a second pulse amplitude to a second electrode combination; and disabling the simultaneous applying of pacing recharge energy when the second pulse amplitude differs from the first pulse amplitude by a specified threshold pulse amplitude difference value.

Example 18 can include subject matter (such as an apparatus), or can optionally be combined with the subject matter of one or any combination of Examples 1-17 to include such subject matter, comprising: a plurality of electrodes implantable at a plurality of tissue sites of a left ventricle and at least one tissue site of a right ventricle of a subject; a stimulus circuit configured to provide electrical cardiac pacing stimulation to multiple combinations of the plurality of electrodes, wherein an electrode combination includes at least a first electrode and a second electrode and the electrical stimulation is selectively applied at the first electrode of the electrode combinations; a recharge circuit including a recharge capacitor electrically coupled to a second electrode of the electrode combinations; a switch circuit configured to enable electrode combinations for electrical coupling to the stimulus circuit and the recharge circuit; and a control circuit including a pacing activation sub-circuit configured to: selectively initiate delivery of the electrical stimulation using multiple electrode combinations; and enable simultaneous delivery of recharge energy from the recharge capacitor to the second electrode of multiple electrode combinations.

In Example 19, the subject matter of Example 18 optionally includes a pacing activation sub-circuit configured to initiate sequential delivery of electrical stimulation pulses to the multiple electrode combinations, and initiate delivery of recharge energy from all of the recharge capacitors simultaneously to all of the second electrodes of the multiple electrode combinations.

In Example 20, the subject matter of Example 18 or Example 19 optionally includes a control circuit is configured to determine a pacing stimulation interval and selectively change the number of recharge capacitors used to simultaneously deliver the pacing recharge energy according to the determined pacing stimulation interval.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a stimulus circuit configured to provide electrical cardiac pacing stimulation to multiple combinations of a plurality of electrodes implantable within a single heart chamber, wherein an electrode combination includes at least a first electrode and a second electrode and the electrical stimulation is selectively applied at the first electrode of the electrode combinations;
   a recharge circuit including one or more recharge capacitors electrically coupled to the second electrode of the electrode combinations;
   a switch circuit configured to selectively enable electrode combinations for electrical coupling to the stimulus circuit and the recharge circuit; and
   a control circuit including a pacing activation sub-circuit configured to: selectively initiate delivery of the electrical stimulation to the single heart chamber using multiple electrode combinations; and enable at least partial simultaneous delivery of pacing recharge energy from the one or more recharge capacitors to the second electrode of the multiple electrode combinations.

2. The apparatus of claim 1, wherein the pacing activation sub-circuit is configured to initiate sequential delivery of electrical stimulation pulses to the multiple electrode combinations, and initiate delivery of pacing recharge energy from all of the recharge capacitors simultaneously to all of the second electrodes of the multiple electrode combinations.

3. The apparatus of claim 1, wherein the control circuit is configured to determine a pacing stimulation interval and selectively change the number of recharge capacitors used to simultaneously deliver the pacing recharge energy according to the determined pacing stimulation interval.

4. The apparatus of claim 1, wherein the control circuit is configured to determine a pacing stimulation interval and selectively enable simultaneous delivery of the pacing recharge energy according to the determined pacing stimulation interval.

5. The apparatus of claim 1, wherein the pacing activation sub-circuit is configured to: initiate delivery of a first electrical stimulation pulse having a first pulse amplitude to a first electrode combination; and initiate sequential delivery of a second electrical stimulation pulse having a second pulse amplitude to a second electrode combination; and wherein the control circuit is configured to disable the simultaneous delivery of pacing recharge energy when the second pulse amplitude differs from the first pulse amplitude by a specified threshold pulse amplitude difference value.

6. The apparatus of claim 1, wherein the pacing activation sub-circuit is configured to: initiate delivery of a first electrical stimulation pulse having a first pulse amplitude and a first pulse width to a first electrode combination; and initiate sequential delivery of a second electrical stimulation pulse having a second pulse amplitude and a second pulse width to a second electrode combination; and wherein the control circuit is configured to determine charge applied to the electrode combinations and disable the simultaneous delivery of pacing recharge energy when charge applied to the second electrode combination differs from the charge applied to the first electrode combination by a specified threshold charge difference value.

7. The apparatus of claim 1, wherein the pacing activation sub-circuit is configured to:
   initiate delivery of a first electrical stimulation pulse having a first pulse amplitude to a first electrode combination;
   initiate sequential delivery of a second electrical stimulation pulse having a second pulse amplitude to a second electrode combination;
   initiate delivery, in a first recharge mode, of the first recharge energy pulse and the second recharge energy pulse simultaneously after the second electrical stimulation pulse when the second pulse amplitude differs from the first pulse amplitude by less than a specified threshold pulse amplitude difference value; and
   initiate delivery, in a second recharge mode, of a first recharge energy pulse to the first electrode combination after the first electrical stimulation pulse, and deliver a second recharge energy pulse to the second electrode combination after the second electrical stimulation pulse when the second pulse amplitude differs from the first pulse amplitude by at least the specified threshold pulse amplitude difference value.

8. The apparatus of claim 1, including an impedance measurement circuit electrically coupled to the switch circuit and configured to generate an impedance signal representative of the impedance of an electrode combination, wherein the control circuit is configured to initiate a measurement of a first impedance of a first electrode combination; initiate a measurement of a second impedance of a second electrode combination; and disable the simultaneous delivery of pacing recharge energy when the first impedance differs from the second impedance by a specified threshold impedance difference value.

9. The apparatus of claim 1, wherein the pacing activation sub-circuit is configured to:
   initiate delivery of multiple sequential electrical stimulation pulses using a first subset of multiple electrode combinations of the plurality of electrodes;
   initiate simultaneous delivery of pacing recharge energy associated with the delivery of electrical stimulation pulses by the first subset of multiple electrode combinations;
   initiate delivery of multiple sequential electrical stimulation pulses using a second subset of multiple electrode combinations of the plurality of electrodes; and
   initiate simultaneous delivery of pacing recharge energy associated with the delivery of electrical stimulation pulses by the second subset of multiple electrode combinations.

10. The apparatus of claim 1, wherein the control circuit is configured to: determine an electrode arrangement electrically coupled to the implantable medical device; and enable the simultaneous delivery of pacing recharge energy from the recharge capacitors according to the determined electrode arrangement.

11. The apparatus of claim 1, including a communication circuit electrically coupled to the control circuit and configured to receive an indication of an electrode arrangement electrically coupled to the implantable medical device, wherein the control circuit is configured to enable the simultaneous delivery of pacing recharge energy from the recharge capacitors according to the indicated electrode arrangement.

12. The apparatus of claim 1, including an implantable cardiac lead incorporating at least a portion of the plurality of electrodes, wherein the recharge circuit is configured to provide recharge energy to at least one combination of electrodes that includes a bipolar electrode pair.

13. The apparatus of claim 1, including a hermetically sealed housing; a can electrode incorporated into the hermetically sealed housing; and an implantable cardiac lead incorporating at least a portion of the plurality of electrodes, wherein the recharge circuit is configured to provide recharge energy to at least one combination of electrodes that includes the can electrode and at least one electrode incorporated into the cardiac lead.

* * * * *